United States Patent [19]
Fahn et al.
[11] 4,072,538
[45] Feb. 7, 1978

[54] PROCESS FOR THE TWO-STAGE DECOMPOSITION OF HEMI-CELLULOSES TO XYLOSE

[75] Inventors: Rudolf Fahn, Gammelsdorf; Bernd Brenner, Moosburg; Hans Buckl, Freising-Tumtenhausen, all of Germany

[73] Assignee: Sud-Chemie AG, Munich, Germany

[21] Appl. No.: 729,058

[22] Filed: Oct. 4, 1976

[30] Foreign Application Priority Data

Oct. 8, 1975 Germany ............................ 2545110

[51] Int. Cl.[2] ........................ C13K 13/00; C13K 1/02; C07C 31/18

[52] U.S. Cl. ......................................... 127/37; 127/1; 260/635 C

[58] Field of Search .................. 127/1, 37; 260/635 C

[56] References Cited

U.S. PATENT DOCUMENTS

| | | | |
|---|---|---|---|
| 3,565,687 | 2/1971 | Suminoe | 127/37 |
| 3,954,497 | 5/1976 | Friese | 127/37 |
| 3,970,712 | 7/1976 | Friese | 127/37 X |
| 3,990,904 | 9/1976 | Friese | 127/37 |
| 4,029,515 | 6/1977 | Kiminki | 127/37 |

*Primary Examiner*—Sidney Marantz
*Attorney, Agent, or Firm*—Burgess, Dinklage & Sprung

[57] ABSTRACT

Process for the two-stage decomposition of hemi-celluloses of xylan-containing natural products for the purpose of obtaining xylose and xylitol where the starting material is treated in the first stage with a basic medium and the obtained solid residue is subjected in a subsequent stage to an acid treatment wherein the alkaline and acid stages are carried out in a single reaction vessel.

19 Claims, 1 Drawing Figure

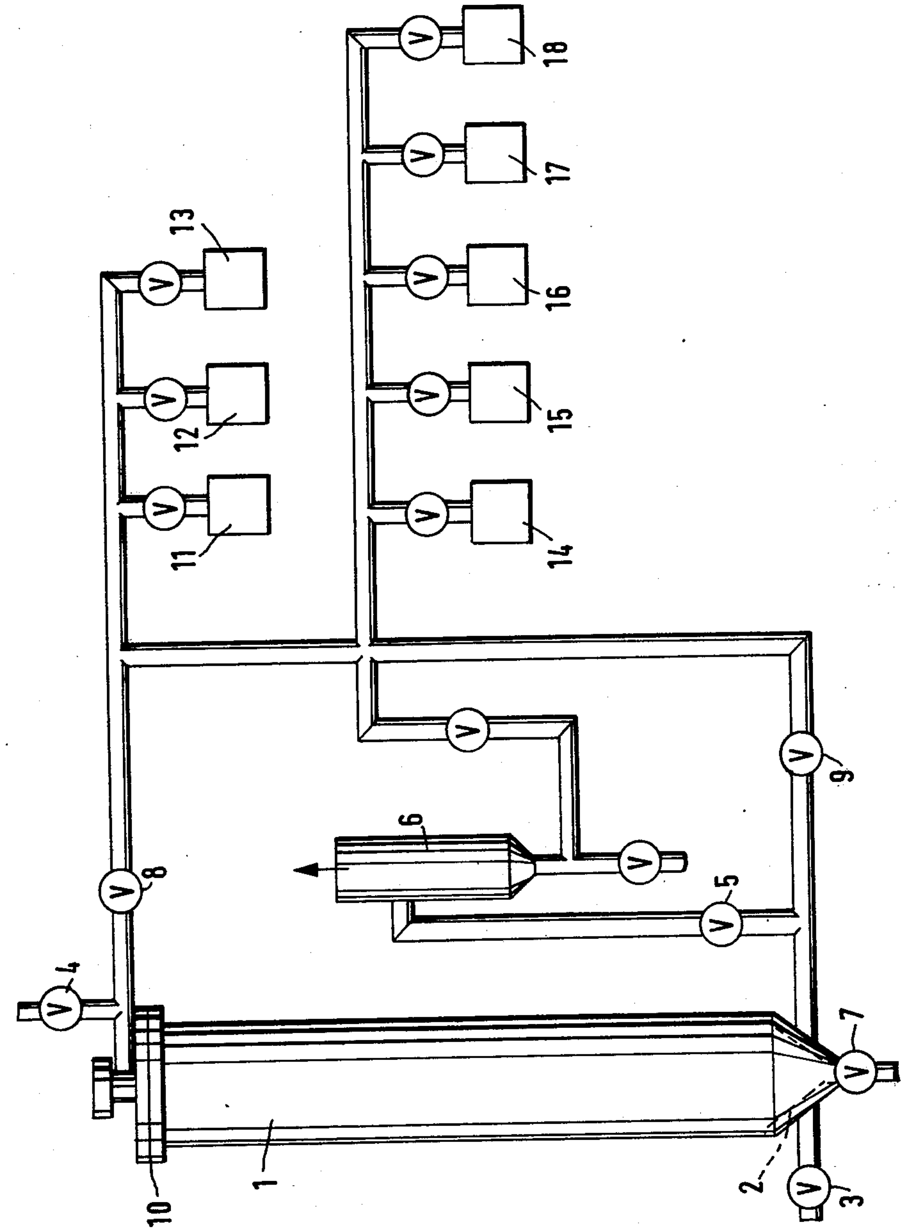
1
2
3
4
5
6
7
8
9
10
11
12
13
14
15
16
17
18
V

PROCESS FOR THE TWO-STAGE DECOMPOSITION OF HEMI-CELLULOSES TO XYLOSE

BACKGROUND OF THE INVENTION

1. Field of the Invention

This invention relates to the recovery of xylose and xylitol products from alkaline and acid treated extracts employed during the treatment of xylan-containing materials, especially hemi-celluloses of xylan-containing natural products. This invention is particularly concerned with maximizing the yield of xylose or xylitol by treatment of acid extract solutions and acid solutions obtained by the treatment of the material and aqueous wash solutions.

2. Discussion of the Prior Art

D-(+) xylose and its hydrogenation product xylitol have an appreciable technical significance. Xylose can be used, for example, in the foodstuffs industry for various purposes, while xylitol has proven to be a very good sweetening agent for diabetics. Almost exclusively leaf-bearing wood types, such as beech and chestnut, are used as starting material for the industrial production of xylose. The yields lie at 10–12% (see for example Ger. Pat. Sp. No. 912,440).

From Ger. Pat. Sp. No. 834,079 the obtaining of xylose from oat husks is known. In this process the oat husks are heated to boiling point with 0.08% ammonia or extracted with a benzene alcohol mixture. Then the used pressure hydrolysis takes place with 0.2 to 0.5% $H_2SO_4$ at 125° C. No further processing takes place.

In the preliminary tratment with $NH_3$, 4 kg of $NH_3$ as 0.08% solution are used on 1000 kg of oat husks. In order to split off the acetic acid, however 17 kg of $NH_3$ would be necessary. Moreover under the conditions stated in the Ger. Pat. Sp. splitting off and thus removal of the acetic acid, which amounts to about 6% of the weight of the oat husks, could hardly take place.

On the basis of this process, in German patent applications Nos. 2,358,407 and 2,358,472, processes are proposed for the production of xylose solutions by decomposition of leaf-bearing wood or oat husks with a basic medium and treatment of the obtained solid residue with mineral acid. These processes, which are characterised in that alkali hydroxide is used as basic medium, firstly permit complete exploitation of the starting material and also produce a higher xylose yield.

In these processes the alkaline decomposition solution must be filtered off from the residue, whereupon the residue must be washed in order to remove the alkali as extensively as possible. An alkali content in the residue would be troublesome in the subsequent acid decomposition. The filtration and washing out of the residue occurring in the alkaline decomposition are carried out in large industrial operation generally with the aid of filter presses, which require relatively large quantities of washing water, so that waste water problems can arise. Moreover the recovery of the acetic acid present as alkali acetate causes difficulties in the case of dilute decomposition and washing solutions.

The residue occurrng in the second stage after the treatment with mineral acid is also ordinarily separated with the aid of filter presses from the acid, xylose-containing decomposition solution, after-washing likewise being necessary. Thus the xylose solutions occur in relatively dilute form, so that the energy consumption in concentration by evaporation becomes relatively great.

It is an object of the present invention to, avoid the disadvantages involved with filter presses, and to provide a process for the two-stage decomposition of hemi-celluloses in which the decomposition solutions are obtained in relatively concentrated form and the quantity of washing water at every stage can be kept to a minimum.

SUMMARY OF THE INVENTION

Thus the object of the invention is a process for the two-stage decomposition of the hemi-celluloses from xylan-containing natural products for the purpose of obtaining xylose, where the starting material is treated in the first stage with a basic medium and the obtained solid residue is subjected in the second stage to an acid treatment; the process is characterised in that the two stages are carried out in one single reaction vessel while a. in the first stage the starting material is treated at standard pressure or elevated pressure and elevated temperature with an alkali-hydroxide solution, the alkali content of which is sufficient to split off and neutralise the acetic acid bound in the starting material, the alkali solution is filtered off from the reaction vessel and the obtained residue is extracted, and b. in the second stage the extraction residue is subjected at elevated pressure and elevated temperature to an acid treatment, the acid solution is filtered off from the reaction vessel and the obtained residue is extracted afresh and in that the solution or extract from the second stage is worked up for the recovery of xylose or xylitol and possibly also the solution or extract from the first stage is worked up for the recovery of organic acids and lignin.

By carrying out the two stages in one single reaction vessel the filter presses usual hitherto can be omitted, that is the residue occurring in the first stage does not need to be transferred from the reaction vessel into a filter press and thence after washing into a second reaction vessel and after the acid decomposition again to be transferred into a filter press. The technical feasibility of the two-stage decomposition in one single reaction vessel seemed practically impossible from the outset, since the layer thickness of the residue to be washed is very high in comparison with the layer thickness of the filter cake in a normal filter press. Moreover some xylan-containing natural products swell in alkaline solutions, so that especially in the first stage with a great layer thickenss of the residue, difficulties had to be expected during filtration. Surprisingly however it was ascertained that the extraction of the alkaline-treated residue after a certain starting time proceeds very rapidly, after the alkali content has been reduced somewhat by the washing water.

Xylan-containing natural products there which may be used are for example wood waste, especially from leaf-bearing wood such as beech, birch or oak wood; oat husks; straw, for example wheat, rye, barley, oat or rice straw etc., maize (corn) cobs, bagasse, nut shells such as coconut shells, almond shells, the shells of palm kernels, olive stones, date stones, babacou nuts and similar nuts. The advantages of the process according to the invention are especially distinct in the case of xylan-containing natural products which display a high tendency to swelling in alkaline solutions, for example oat husks and straw.

Ordinarily the alkali treatment will be carried out in the first stage at a pressure of about 1.0 to 3.0 bar, preferably about 1.5 to 2.0 bar, at temperatures of about 80° to 150° C, preferably 100° to 120° C, and during a time of about 30 to 120, preferably about 60 minutes; the obtained solution is filtered off from the reaction vessel preferably at temperatures of about 100° to 150° C. Naturally lower temperatures can also be used, in which case admittedly longer times are necessary in order to split off the bound acetic acid. On the other hand at higher temperatures there is danger of destruction of the pentosans. The concentration of the alkali hydroxide solution in the first stage also influences the decomposition time and the destruction of the pentosans, for which reason an approximately 0.025 to 1.25 molar alkali hydroxide solution is preferably used. With higher alkali hydroxide concentrations it is also possible for example for soluble lignin-xylose complexes to form which lead to a reduction of the xylose yield.

By the use of alkali hydroxide in the first stage of the process according to the invention the bound acetic acid contained in the utilised xylan-containing natural products is split off and neutralised, if at least one mol of alkali is used per mol of bound acetic acid. Moreover the crystallisation-inhibiting nitrogen-containing substances and other accompanying substances, regarding the nature of which nothing is yet known, pass into solution while the pentosan is not attacked by the alkali hydroxide in the utilised concentration. The acetic acid bound to the alkali can be liberated by acidulation and distilled off and, if desired, recovered from the distillate by extraction with a suitable solvent.

One preferably used 1 to 2 mol of alkali hydroxide per mol of bound acetic acid, especially 1.1 to 1.2 mol of alkali hydroxide per mol of bound acetic acid. When alkali hydroxide is used in a quantity of about 2 mol, the destruction of the pentosans and thus a reduction of yield of xylose makes itself noticeable. The quantity of bound acetic acid can easily be ascertained by an experimental decomposition.

An especially preferred feature of the invention consists in that the extraction after the alkali treatment is carried out with at least one liquid surge at a temperature of about 20° to 120° C preferably about 50° to 100° C. By "liquid surge" there is understood the intermittent introduction of relatively small volumes of solvent into the reaction vessel, in contrast with a constant stream of solvent. The introduced quantity of solvent is usually not higher than the volume of the residue to be extracted. After the introduction of the solvent or extraction medium this remains in stationary contact with the residue to be extracted for a specific time, is then forced out of the residue by pressure difference and then replaced by a second liquid surge, the volume of which likewise lies approximately in the order of magnitude of the volume of the residue to be extracted.

The extraction after the alkali treatment is preferably carried out in several liquid surges, one of the last surges being adjusted by means of acid to a pH value below 5. This has the advantage that in the subsequent acid treatment the acid concentration is maintained.

Ordinarily the acid treatment will be carried out at temperature of about 100° to 150° C, preferably about 120° to 140° C, the quantity of acid in general being dimensioned so that it is just absorbed by the extraction residue of the first stage. Here either a precisely measured quantity of acid can be introduced into the reaction vessel, or, which is simpler, firstly the acid can be supplied in excess and the excess can be filtered off. The limitation of the quantity of acid has the advantage that the decomposition takes place in a protective manner, that is to say only the hemi-celluloses are decomposed, and the undesired formation of furfurol is reduced, so that higher xylose yields are obtained.

The acid treatment is ordinarily carried out with dilute mineral acid, although organic acids such as oxalic acid can also be used. As mineral acids there are used for example $H_2SO_4$, HCl or HBr, but preferably $H_2SO_4$ in a concentration of about 0.5 to 5% by weight, the treatment time amounting to about 15 to 45 minutes in this case.

As in the extraction after the alkali treatment, the extraction after the acid treatment is preferably also carried out with at least one liquid surge at a temperature of about 20° to 120° C, preferably about 50° to 100° C, the advantages set forth above in connection with the alkaline extraction being achieved. An additional advantage is achieved by the fact that as a result of the relatively small volumes of extraction liquid, higher xylose concentrations are maintained so that the processing of the xylose solutions becomes more economical. The alkali and/or acid treatment and possibly the subsequent extraction (this applies both to the extraction after the alkali treatment and to the extraction after the acid treatment) are preferably carried out with less concentrated extracts from previous batches. In this way the dissolved substances present in the less concentrated extracts are not lost, but are constantly further re-concentrated. This is especially important for the second stage, since in this way the xylose losses can be kept low.

It has further proved advantageous to supply steam during the alkali and/or acid treatment, possibly also during the subsequent extractions. The steam serves for heating or for maintenance of the temperature in the reaction vessel, whereby especially the rate of extraction is raised. It is especially advantageous to supply the steam during the alkali treatment, since in this way the filtering off of the basic extract and the subsequent washing of the residue are facilitated.

Due to the supply of steam in the alkali and/or acid treatment and possibly in the subsequent extractions, the starting material and the residue are preheated to a temperature of about 100° to 150° C. This measure leads not only to an improved filtration or washing effect, but in combination with the measure that a liquid colder by about 10° to 60° C. is suddenly added to the preheated starting material and residue, to the further advantage that the steam condenses in the pores of the starting material and residue and due to the occurring vacuum the colder liquid is sucked into the pores, in this way the substance exchange is improved.

The treatment solutions and extracts are filtered through a sieve arranged in the lower part of the reaction vessel, and processed.

BRIEF DESCRIPTION OF DRAWINGS

Referring to the accompanying drawing, the same shows a flow diagram of the process of the invention representing a preferred mold for carrying out the process.

EXAMPLE

In order to more fully understand the nature of the invention and the manner of practicing the same, the following example is presented.

EXAMPLE 20 kg of oat husks with about 10% moisture content are charged into a pressure vessel 1 with built-in lower sieve cone 2, heated by charging of steam from beneath (valve 3) through the sieve cone 2 to about 110° C, whereby a pressure of about 1.5 bar establishes itself, and then steamed for 10 minutes with vent valve 4 slightly open. Then 60 liters of aqueous caustic soda with a concentration of about 0.5 to 1.0% by weight of NaOH are charged from above with a temperature of about 60° C. from the container 11 through the valve 8, and heating to 110° C. is effected again.

By charging of steam from beneath through the valve 3 with the vent valve 4 slightly opened, the liquid-solid mixture is kept at this temperature for an hour; then the caustic soda not taken up by the material is let off with the extract substances through the valve 5 by way of the sieve cone 2, expanded to atmospheric pressure in the expansion container 6 and supplied for further treatment (recovery of the acetic acid).

For the extraction, 40 liters of water with a temperature of 90° C. are charged from the container 12 from above as a surge and heating is effected from beneath through the valve 3 by charging of steam, to at least 110° C. The obtained extract is conducted away through the sieve cone 2, the valve 5 and the expansion container 6 for further treatment or processing for the obtaining of organic acids (for example acetic acid) and lignin or for storage for the purpose of re-use.

Three further water surges of 20 liters and 90° C. follow analogously from the container 12. Then 20 liters of 0.05% sulphuric acid at 90° C. are charged from the container 13 and thereafter again 20 liters of water at 90° C. from the container 12. In order to arrive at a higher concentration, the last surges can be stored and used in the next batch for the starting of the caustic soda or as first washing surges.

The residue remaining after the extraction of the alkaline-treated starting material is heated to 110° C. in the same pressure vessel 1. A pressure of about 1.5 bar then establishes itself. From the container 14 in all 50 liters of 2.5% sulphuric acid at 60° C. are charged, namely 25 liters from above and 25 from beneath, by means of the valves 8 and 9 respectively. After the impregnation of the extraction residue the dilute acid is let off through the sieve cone 2 and the expansion container 6 into the container 14. There the acid after concentration to an $H_2SO_4$ content of 2.5% is stored for the following batch. The filling is now heated up by direct steam to 135° C. corresponding to 3.5 bar and left for 30 minutes at this temperature.

20 liters of stored extract from a previous acid-treated batch with a temperature of about 90° C. are charged from the container 15 from above through the valve 8, for the extraction and the filling is brought with direct steam from beneath through the valve 3 to 110° C. The obtained extract is withdrawn through the sieve cone 2 and the expansion container 6. The obtained solution with a xylose concentration of about 15% and little impurities can be processed into xylose and possibly to xylitol. The total yield of xylose in the extract (in relation to the xylose content of the starting material) amounts to 80%.

In an analogous manner the charging of the next two washing surges takes place in each case with about 15 liters of liquid at about 90° C. from the containers 16 and 17, which liquid after withdrawal from the pressure vessel 1 is stored in the container 15 for the next batch. The next surge is taken from the container 18 and stored in the container 16, the last two surges (about 15 liters each) consist of water at about 60° C. from the container 12.

These surges are stored in the containers 17 and 18. The pressure vessel 1 is again heated up to a temperature corresponding to 4 bar and the residue is expelled through the valve 7. It amounts to 50% of the introduced dry substance and has a moisture content of about 65%. A new filling can be charged after the opening of the upper closure 10.

What is claimed is:

1. In a process for the two-stage decomposition of a hemi-cellulose of a xylan-containing natural product for the purpose of obtaining xylose wherein the hemi-cellulose of xylan is treated in a first stage with a basic medium and the obtained solid residue is thereafter subjected in a subsequent stage to an acid treatment, the improvement wherein the treatment with said basic medium and said acid are carried out in a single reaction vessel and:
   - a. in the first stage the hemi-cellulose of xylan-containing material is treated at an atmospheric or elevated pressure and at an elevated temperature with an alkali hydroxide solution, the alkali content of which is sufficient to split off and neutralize acetic acid bound in the hemi-cellulose of the xylan-containing material, and the resultant alkaline solution is filtered off from the reaction vessel to leave behind the solid residue;
   - b. following the alkali treatment, the solid residue is extracted within the reaction vessel with at least one liquid surge at a temperature of about 20 to 120° C;
   - c. in the subsequent stage the so-extracted solid residue is subjected at an elevated pressure and at an elevated temperature to an acid treatment, the acid treatment being effected employing an acid solution, said acid solution being filtered off following contact with said solid extraction residue from the reaction vessel;
   - d. the resultant acid treated residue is extracted afresh within the reaction vessel with at least one liquid surge at a temperature of about 20° to 120° C;
   - e. the extract obtained from said extraction and the solution obtained from the acid treatment are processed for the recovery of xylose or xylitol.

2. A process according to claim 1 wherein said subsequent stage is a second stage following extraction of the solid residue obtained from said first stage.

3. A process according to claim 1 wherein the alkaline solution filtered off from the reaction vessel is processed for the recovery of organic acids and lignin.

4. A process according to claim 1 wherein the contact with the liquid surge is conducted at a temperature of 50° to 100° C.

5. A process according to claim 1 wherein the extraction following the alkali treatment is carried out in several liquid surges and at least one of the surges has a pH value below 5.

6. A process according to claim 1 wherein the extraction following the acid treatment is carried out at a temperature of about 50° to 100° C.

7. A process according to claim 1 wherein the alkali and/or acid treatment is carried out with less concentrated extracts obtained from preceding batches.

8. A process according to claim 1 wherein steam is supplied during the alkali and/or acid treatment.

9. A process according to claim 8 wherein steam is also applied during the subsequent extractions following the alkali or acid treatment.

10. A process according to claim 1 wherein the alkali and/or acid treatment is conducted employing a material which is preheated to a temperature of 100° to 150° C.

11. A process according to claim 10 wherein following the preheating of the starting material to 100° to 150° C a liquid cooler is suddenly added thereto which is cooler by about 10° to 60° C than the heaed starting material.

12. A process according to claim 1 wherein the alkali treatment is carried out at a pressure of 1.0–3.0 bar at a temperature of 80° to 150° C for a period of time of 30 to 120 minutes and the resultant solution is filtered off in the reaction vessel at a temperature of 100° to 150° C.

13. A process according to claim 12 wherein the alkali treatment is effected at a pressure of 1.5 to 2.0 bar, at a temperature of 100° to 120° C for a period of time of about 60 minutes.

14. A process according to claim 12 wherein the alkali treatment is carried out employing an approximately 0.025 to 1.25 molar alkali hydroxide solution.

15. A process according to claim 1 wherein the acid treatment is carried out at a temperature of about 100° to 150° C, the quantity of acid being so dimensioned that it is just taken up by the solid extraction residue from the alkali treatment.

16. A process according to claim 15 wherein the acid treatment is carried out at a temperature of 120° to 140° C.

17. A process according to claim 15 wherein the acid treatment is carried out with a dilute mineral acid.

18. A process according to claim 17 wherein the dilute mineral acid is 0.5 to 5 weight percent sulfuric acid solution.

19. A process according to claim 17 wherein the acid treatment is carried out for a period of time of 15 to 45 minutes.

* * * * *